United States Patent
Lai et al.

(10) Patent No.: US 9,789,434 B1
(45) Date of Patent: Oct. 17, 2017

(54) SYSTEMS AND METHODS FOR GAS PRE-SEPARATION FOR DETECTION OF SUBSTANCES

(71) Applicant: Morpho Detection, LLC, Newark, CA (US)

(72) Inventors: Hanh T. Lai, Arlington, MA (US);
Vibha Mishra, Woburn, MA (US);
Wilhelm P. Platow, Newburyport, MA (US)

(73) Assignee: Morpho Detection, LLC, Newark, CA (US)

( * ) Notice: Subject to any disclaimer, the term of this patent is extended or adjusted under 35 U.S.C. 154(b) by 0 days.

(21) Appl. No.: 15/082,108

(22) Filed: Mar. 28, 2016

(51) Int. Cl.
| | |
|---|---|
| *G01N 30/60* | (2006.01) |
| *G01N 30/62* | (2006.01) |
| *G01N 33/22* | (2006.01) |
| *G01N 1/22* | (2006.01) |
| *B01D 53/02* | (2006.01) |
| *G01N 30/72* | (2006.01) |
| *G01N 33/00* | (2006.01) |

(52) U.S. Cl.
CPC ....... *B01D 53/025* (2013.01); *G01N 30/6078* (2013.01); *G01N 33/227* (2013.01); *G01N 1/2202* (2013.01); *G01N 1/2214* (2013.01); *G01N 1/2273* (2013.01); *G01N 30/7206* (2013.01); *G01N 33/0022* (2013.01); *G01N 33/0057* (2013.01); *Y10T 436/173076* (2015.01); *Y10T 436/25375* (2015.01); *Y10T 436/25875* (2015.01)

(58) Field of Classification Search
CPC ...... G01N 1/22; G01N 1/2202; G01N 1/2214; G01N 1/2273; G01N 30/02; G01N 30/6078; G01N 30/72; G01N 30/7206; G01N 33/0004; G01N 33/0021; G01N 33/0022; G01N 33/0057; G01N 33/22; G01N 33/227; Y10T 436/17; Y10T 436/170769; Y10T 436/173076; Y10T 436/25; Y10T 436/25375; Y10T 436/25875
USPC ....... 436/106, 107, 110, 147, 161, 171, 173, 436/174, 177, 181; 422/89, 527
See application file for complete search history.

(56) References Cited

U.S. PATENT DOCUMENTS

| | | | |
|---|---|---|---|
| 5,736,739 | A | 4/1998 | Uber et al. |
| 7,520,159 | B2 | 4/2009 | Paakkanen et al. |
| 7,608,818 | B2 | 10/2009 | Miller et al. |
| 8,117,895 | B2 | 2/2012 | Currie et al. |

(Continued)

FOREIGN PATENT DOCUMENTS

| | | |
|---|---|---|
| DE | 4443754 A1 | 6/1996 |
| WO | 9714957 A1 | 4/1997 |
| WO | 2006119167 A1 | 11/2006 |

OTHER PUBLICATIONS

Buryakov et al. Journal of Analytical Chemistry, vol. 58, No. 10, 2003, pp. 944-950.*

(Continued)

*Primary Examiner* — Maureen Wallenhorst
(74) *Attorney, Agent, or Firm* — Armstrong Teasdale LLP

(57) ABSTRACT

The present disclosure is directed to methods and systems for detecting a substance in a sample gas. The methods and systems include separating the substance of interest in the sample gas, and introducing the separated sample gas into a detector. The systems and methods further include performing an analysis of the substance of interest.

19 Claims, 6 Drawing Sheets

(56) References Cited

U.S. PATENT DOCUMENTS

| | | |
|---|---|---|
| 8,841,611 B2 | 9/2014 | Li et al. |
| 2004/0031919 A1 | 2/2004 | Leonhardt et al. |
| 2007/0029477 A1 | 2/2007 | Miller et al. |
| 2007/0256474 A1* | 11/2007 | Paakkanen ............. B01D 53/02 73/23.37 |
| 2014/0151546 A1* | 6/2014 | Li ........................ H01J 49/062 250/282 |

OTHER PUBLICATIONS

Buryakov, Igor A., "Express Analysis of Explosives, Chemical Warfare Agents and Drugs with Multicapillary Column Gas Chromatography and Ion Mobility Increment Spectrometry", Journal of Chromatography B, 2004, vol. 800: Nos. 1-2, pp. 75-82.

Gruznov et al., Gas Analytical Technologies for Physical Protection of Oil and Gas Objects:, Strategic Insights, Feb. 2008, vol. VII, Issue 1, 10 pages.

Perl et al., "Alignment of retention time obtained from multicapillary column gas chromatography used for VOC analysis with ion mobility spectrometry", Anal Bioanal Chem, 2010, vol. 397, pp. 2385-2394.

Xie et al., "A novel Method for the Detection of MTBE: Ion Mobility Spectrometry coupled to Multi Capillary Column" IJIMS, 2000, vol. 4, No. 1, pp. 77-83.

Anonymous, "MCC applications (portable GC)", Apr. 20, 2009, retrieved from the Internet: URL:http://www.mcc-chrom.com/ftpgetfile.php?id=22, 4 pages.

Baumbach, Jörg Ingo, "Ion mobility spectrometry coupled with multi-capillary columns for metabolic profiling of human breath", IOP Publishing, J. Breath Res., 2009, vol. 3, No. 3, 16 pages.

European Search Report for EP 17 00 0502, dated Aug. 4, 2017, 8 pages.

\* cited by examiner

SYSTEMS AND METHODS FOR GAS PRE-SEPARATION FOR DETECTION OF SUBSTANCES

BACKGROUND OF THE DISCLOSURE

The embodiments described herein relate generally to a detection technique for chemical substances, and, more particularly, to separating components of a sample gas prior to introducing the sample gas into a detector. More specifically, the methods and systems include using a multi-capillary column (MCC) separation device to temporally separate a substance of interest in the sample gas. The systems and methods further include performing an analysis of the separated substance of interest to detect the substance of interest.

Certain contraband substances—such as explosive or narcotics—are difficult to detect in trace amounts. In some cases, environmental interferents reduce detection of these substances of interest. In other cases, a detector mistakenly identifies an environmental interferent as a contraband substance. In some known systems, a membrane inlet is employed at a detector inlet to reduce the problem of environmental interference. However, such membranes not only block out the interferents, but also some portion of the substances of interest, thereby, reducing the detector's overall sensitivity. In other known systems, a single-capillary gas chromatography column is employed to perform gas phase separation of a sample prior to introducing the sample into the detector. However, the long single-capillary column often requires a very long separation time and limits the detector to a low gas flow rate. Such systems are not suitable for applications that require high throughput and large gas volume input. Some such systems provide the single capillary column in a coiled arrangement within a large, bulky oven to heat the column to higher temperatures for sample separation, but such ovens are not practical for use in applications where space may be limited.

BRIEF DESCRIPTION OF THE DISCLOSURE

In one embodiment of the present disclosure, a method for detecting a substance of interest is disclosed. The method includes collecting a sample including at least one substance of interest, and introducing the sample into a separation device, wherein the separation device includes a multi-capillary column (MCC). The method also includes separating the at least one substance of interest within the MCC, and transferring the at least one separated substance of interest into a detector. The at least one separated substance of interest is transferred into the detector at a flow rate of from about 10 ml/min to about 500 ml/min. The method further includes performing an analysis of the at least one separated substance of interest, and detecting the at least one substance of interest.

In another embodiment of the present disclosure, a system for detecting a substance of interest is disclosed. The system includes a sample inlet configured to receive a sample including at least one substance of interest. The system also includes a multi-capillary column (MCC) separation device, the MCC separation device coupled in flow communication with the sample inlet and configured to separate the at least one substance of interest. The system further includes an analysis device coupled in flow communication with the MCC separation device. The analysis device is configured to receive the at least one separated substance of interest and perform an analysis of the at least one separated substance of interest, wherein the MCC separation device is configured to transfer the at least one separated substance of interest into the analysis device at a flow rate of from about 10 ml/min to about 500 ml/min.

In yet another embodiment of the present disclosure, a system for detecting a substance of interest is disclosed. The system includes a sample inlet configured to receive a sample including at least one substance of interest. The system also includes an analysis device including a multi-capillary column (MCC) separation device located therein. The MCC separation device is coupled in flow communication with the sample inlet and configured to separate the at least one substance of interest. The analysis device is configured to perform an analysis of the at least one separated substance of interest, wherein the MCC separation device is configured to transfer the at least one separated substance of interest from the sample at a flow rate of from about 10 ml/min to about 500 ml/min.

In still another embodiment of the present disclosure, a method for detecting a substance of interest is disclosed. The method comprises separating at least one substance of interest from a sample, wherein the at least one substance of interest is separated in a multi-capillary column (MCC); transferring the at least one separated substance of interest into a detector, wherein the at least one separated substance of interest is transferred into the detector at a flow rate of from about 10 ml/min to about 500 ml/min, wherein the detector performs an analysis of the at least one separated substance of interest and detects the at least one substance of interest.

DETAILED DESCRIPTION OF THE DISCLOSURE

Figure 1:
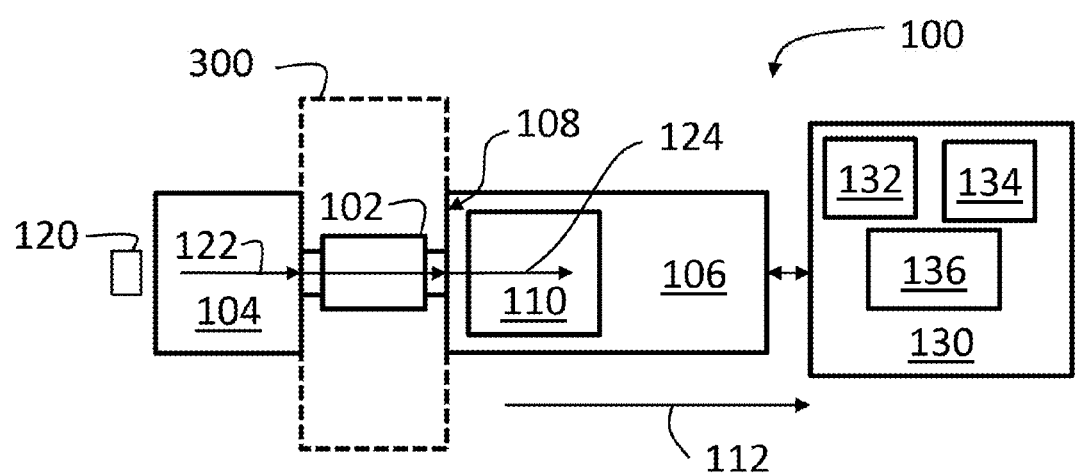
FIG. 1 is an exemplary embodiment of a schematic diagram of a detection system including an MCC separation device in accordance with the present disclosure.

The embodiments disclosed herein improve detection of substances of interest (e.g., explosives) through the use of a multi-capillary column (MCC) gas chromatography separation device to temporally separate the substances of interest. In particular, a sample is introduced to a sample inlet and transferred to the MCC separation device for separation of a substance of interest from other components of the sample. This method of pre-separation reduces environmental sample interference. The MCC separation device then introduces the separated sample into a detector for analysis thereof.

The present disclosure is directed to separating components of a sample gas using an MCC separation device prior to transferring the sample gas to a detector. In particular, the MCC separation device temporally separates a substance of interest from other components of the sample gas. As used herein, "temporally separate" means that the substance of interest is separated from the sample relative to time, such that the substance of interest and the remaining portion of the sample will enter the detector at different times and/or have different drift times within the detector. In some embodiments, the sample includes more than one substance of interest and each substance of interest is temporally separated from each other as well as from any remaining components in the sample, such that each substance of interest will enter the detector at a different time and/or have a different drift time within the detector than the other substance(s) of interest, as well as the remaining components within the sample, if any.

In some embodiments, the MCC separation device separates a substantially non-volatile substance of interest. As defined herein, the term "substantially non-volatile" includes both substances that completely lack volatility (i.e., are non-volatile) and substances that have a low volatility. Volatility is defined as a substance's ability to transform from a solid state to a gaseous state (i.e., vaporized). In some embodiments, a "low volatile" compound includes a compound that is not vaporized at room temperature. In other embodiments, a "low volatile" compound includes a compound that is not vaporized at a temperature of at least about 100° C., at least about 200° C., at least about 300° C., at least about 400° C., at least about 500° C., at least about 600° C. or at least about 700° C. In some embodiments, a "low volatile" compound includes a compound having a vapor pressure of about $10^{-11}$ Torr or below.

In some embodiments of the present disclosure, the substantially non-volatile substance of interest includes at least one of an explosive, an energetic material, a taggant, a narcotic, a toxin, a chemical warfare agent, a biological warfare agent, a pollutant, a pesticide, a toxic industrial chemical, a toxic industrial material, a homemade explosive, a pharmaceutical trace contaminant, a biomarker for medical applications, a chemical marker for medical applications, a biomarker for clinical hygienic applications, a chemical marker for clinical hygienic applications, and/or combinations thereof. In one embodiment of the disclosure, the substance is a nitro-based substance, such as, for example, a nitro-based explosive. In some embodiments, the nitro-based substance includes at least one of nitro, nitrate, triacetone triperoxide (TATP), ammonium nitrate (AN), ammonium nitrate fuel oil (ANFO), urea nitrate (UN), 2,4,6-trinitrophenylmethylnitramine (tetryl), trinitrotoluene (TNT), ethylene glycol dinitrate (EGDN), nitroglycerin (NG), pentaerythritol tetranitrate (PETN), high melting explosive (HMX), Research Department Explosive (RDX), black powder, cocaine, 3,4-methylenedioxy-N-methylamphetamine (MDMA), an opiate, diazepam and combinations thereof.

In some embodiments, a sample of the substance of interest is obtained using a fresh sampling swab. The swab is used to wipe a surface of an object including the substance of interest to collect the sample of the substance of interest. Any quantity of substance of interest is obtained as the sample so long as the sample includes enough of the substance of interest to allow for spectrometric analysis of the sample. In some embodiments, a carrier gas is introduced into the sample inlet and/or into the MCC separation device to carry the sample of the substance of interest through the MCC separation device and into the detector. It should be understood that the carrier gas containing the sample including the substance of interest is referred to herein as the "sample gas" or "sample." In some embodiments, the carrier gas includes at least one of air, hydrogen, a noble gas, oxygen, nitrogen and carbon dioxide. In some embodiments, the air is prepared through drying and scrubbing before it is introduced into the sample inlet and/or into the MCC separation device. The air is cleaned, for example, via pumping the air through a pump and using a desiccant to remove moisture from the air.

Compared to single-column separation devices—which are limited to separating samples at low flow rates (e.g., less than 1 ml/min)—the MCC separation device disclosed herein introduces the separated sample gas to the detector at a higher flow rate. In some embodiments, the MCC separation device transfers the separated substance of interest to the detector at a flow rate of from about 10 ml/min to about 500 ml/min. In other embodiments, the MCC separation device transfers the separated substance of interest to the detector at a flow rate of from about 10 ml/min to about 400 ml/min, from about 10 ml/min to about 300 ml/min, from about 10 ml/min to about 200 ml/min, from about 10 ml/min to about 150 ml/min, from about 20 ml/min to about 500 ml/min, from about 20 ml/min to about 400 ml/min, from about 20 ml/min to about 300 ml/min, from about 20 ml/min to about 200 ml/min, from about 50 ml/min to about 500 ml/min, from about 50 ml/min to about 400 ml/min, from about 50 ml/min to about 300 ml/min, or from about 50 ml/min to about 200 ml/min. In preferred embodiments, the MCC separation device transfers the separated substance of interest to the detector at a flow rate of from about 50 ml/min to about 200 ml/min.

Moreover, compared to single-column separation devices, which also operate under small sample-volume limits, the MCC separation device disclosed herein enables separation of large sample volumes. Enabling an increase in sample volume improves sensitivity of the detection system.

In some embodiments, the detector of the present disclosure (also referred to herein as an "analysis device") includes at least one of an ion mobility spectrometer (IMS), an ion trap mobility spectrometer (ITMS), a drift spectrometer (DS), a non-linear drift spectrometer, a field ion spectrometer (FIS), a radio frequency ion mobility increment spectrometer (IMIS), a field asymmetric ion mobility spectrometer (FAIMS), an ultra-high-field FAIMS, a differential ion mobility spectrometer (DIMS) and a differential mobility spectrometer (DMS), a traveling wave ion mobility spectrometer, a semiconductor gas sensor, a Raman spectrometer, a laser diode detector, a mass spectrometer (MS), an electron capture detector, a photoionization detector, a chemiluminescence-based detector, an electrochemical sensor, an infrared spectrometer, a lab-on-a-chip detector and combinations thereof.

Different substances of interest have different levels of volatility. Substances that are substantially non-volatile do not readily transform from their solid state to their vaporized form, and, as such, detection systems need to be operated at higher temperatures in order to vaporize the substantially non-volatile substances. In some embodiments of the present disclosure, the MCC separation device and the detector are in thermal communication (i.e., are not thermally isolated from each other). In other embodiments, the MCC separation device and the detector are thermally isolated from each other. In some embodiments, separation of the sample gas is performed in a substantially isothermal environment. In these embodiments, the MCC separation device is maintained at a temperature between about 20° C. and about 300° C., between about 20° C. and about 250° C., or between about 20° C. and about 200° C. In some embodiments, the MCC separation device is maintained at a temperature between about 25° C. and about 200° C., or between about 20° C. and about 150° C. In some embodiments, the detector is maintained at the same temperature as the MCC separation device for analysis of the separated sample gas. In some embodiments, the detector is maintained at a different temperature than the MCC separation device for analysis of the separated sample gas.

In other embodiments, separation of the sample gas is performed in a non-isothermal environment. In such embodiments, the MCC separation device is heated from an initial or first temperature of about 20° C. (or "room temperature") to a subsequent or second temperature between about 25° C. and about 300° C., between about 50° C. and about 300° C., between about 50° C. and about 250° C., or between about 25° C. and about 250° C. In some embodiments, the detector is heated to the same temperature as the MCC separation device for analysis of the separated sample gas. In some embodiments, the detector is heated to a different temperature than the MCC separation device for analysis of the separated sample gas. In some embodiments of the present disclosure, the temperature increase occurs over a period of time of from about 0 seconds to about 20 seconds, from about 5 seconds to about 15 seconds, or of about 10 seconds. In some embodiments, after analysis of the separated sample gas, the MCC separation device is cooled from the second temperature to the first temperature. In some embodiments, the MCC separation device is cooled from the second temperature to a third temperature different from the first temperature, such as between about 25° C. and about 250° C., between about 50° C. and about 250° C., between about 50° C. and about 200° C., or between about 25° C. and about 200° C. In some embodiments of the present disclosure, the temperature decrease occurs over a period of time of from about 0 seconds to about 20 seconds, from about 5 seconds to about 15 seconds, or of about 10 seconds.

In some embodiments, the method includes using an ionization source to ionize the separated sample gas within the detector. The ionization source is any ionization system that enables operation of the methods and systems as described herein, including, without limitation, a radioactive ionization source, an electrospray ionization source (ESI), an atmospheric pressure chemical ionization (APCI) source, an atmospheric pressure photoionization (APPI) source, an atmospheric pressure glow discharge (APGD) source, a direct analysis in real time (DART) source, and an atmospheric pressure dielectric barrier discharge (APDBD) source. In some embodiments of the present disclosure, the ionization source comprises at least one of an APCI source, an APPI source, an ESI source and a DART source. Some embodiments of the present disclosure are configured to operate at sub-atmospheric pressures. Such embodiments include an ionization source that is, without limitation, a chemical ionization (CI) source, a photoionization (PI) source, a glow discharge (GD) source, a dielectric barrier discharge (DBD) source and combinations thereof.

In some embodiments, a method for detecting a substance of interest is disclosed, the method includes collecting a sample including at least one substance of interest; introducing the sample into a separation device, wherein the separation device includes a multi-capillary column (MCC); separating the at least one substance of interest within the MCC; transferring the at least one separated substance of interest into a detector, wherein the at least one separated substance of interest is transferred into the detector at a flow rate of from about 10 ml/min to about 500 ml/min; performing an analysis of the at least one separated substance of interest; and detecting the at least one substance of interest.

In some embodiments, the method comprises separating at least one substance of interest from a sample, wherein the at least one substance of interest is separated in a multi-capillary column (MCC); transferring the at least one separated substance of interest into a detector, wherein the at least one separated substance of interest is transferred into the detector at a flow rate of from about 10 ml/min to about 500 ml/min, wherein the detector performs an analysis of the at least one separated substance of interest and detects the at least one substance of interest.

Figure 2:
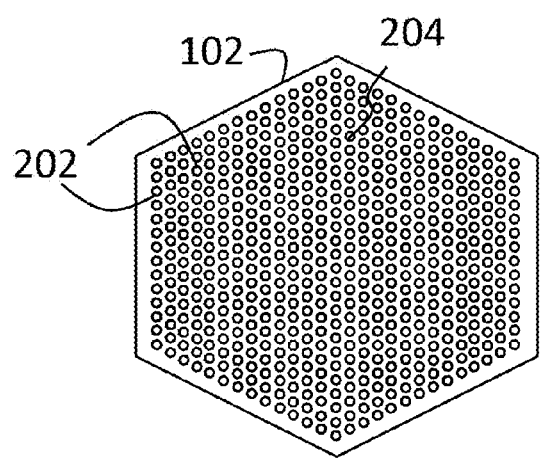
FIG. 2 is a simplified cross-sectional diagram of an exemplary embodiment of the MCC separation device shown in FIG. 1.
Figure 3:
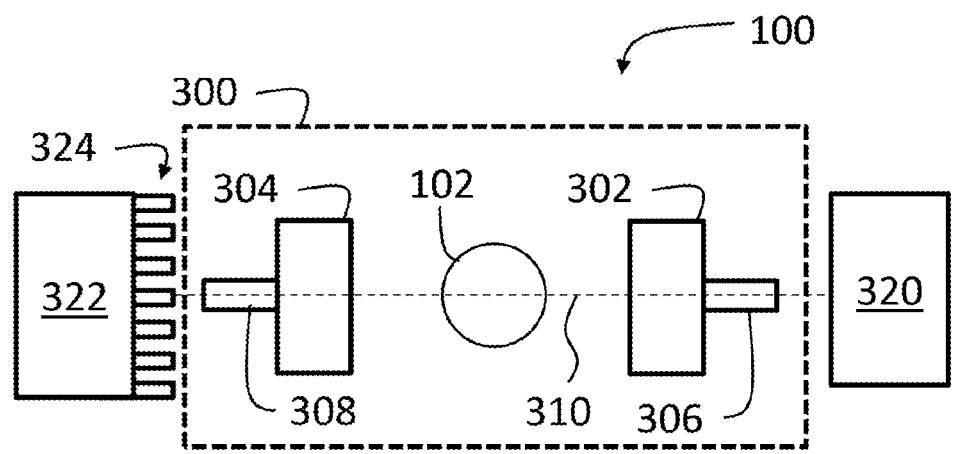
FIG. 3 is an alternative view of the detection system shown in FIG. 1, including a heating and cooling module in accordance with the present disclosure.

FIG. 1 is an exemplary embodiment of a schematic diagram of a detection system 100 including a multi-capillary column (MCC) separation device 102 in accordance with the present disclosure. FIG. 2 is a simplified cross-sectional diagram of an exemplary embodiment of MCC separation device 102 in accordance with the present disclosure. FIG. 3 is an alternative view of detection system 100 of FIG. 1, including a heating/cooling module 300 in accordance with the present disclosure. With continued reference to FIGS. 1-3, detection system 100 includes a sample inlet 104, MCC separation device 102, and a detector 106. In the illustrated embodiment, detector 106 includes a detector inlet 108 and a reaction chamber 110. Furthermore, detector 106 includes a computing device 130 integral thereto and/or otherwise associated therewith. Detection system 100 further includes heating/cooling module 300 configured to heat/cool MCC separation device 102. Heating/cooling module 300 includes a hot block 302 and a cold block 304, as well as a first linear actuator 306 and a second linear actuator 308.

MCC separation device 102 includes a plurality of capillaries 202 coupled together therein. For example, in some embodiments, MCC separation device includes at least 1,000 capillaries 202, at least 500 capillaries 202, at least three hundred capillaries 202, at least one hundred capillaries 202, at least fifty capillaries 202, at least ten capillaries 202, or at least two capillaries 202. Compared to single-capillary column separation devices, MCC separation device 102, with its plurality of capillaries 202, permits faster sample separation. Moreover, the plurality of capillaries 202 in MCC separation device 102 enable separation of larger sample volumes than single-capillary columns. In some embodiments, each capillary 202 is fabricated from a fused silica and/or from any other suitable material. Furthermore, each capillary 202 includes an inner surface 204 and an outer surface 206. Inner surface 204 includes a stationary, liquid-phase film. The film includes, in certain embodiments, dimethyl polysiloxane, polyethylene glycol, and/or any other suitable film.

In one exemplary embodiment, capillaries 202 are arranged parallel to one another. In another exemplary embodiment, capillaries 202 are aligned but other than parallel with one another. In some embodiments, capillaries 202 are straight, coiled, curved, and/or otherwise shaped within MCC separation device 102. In some embodiments, capillaries 202 have a length of between about 1 cm and about 35 cm, between about 2 cm and about 20 cm, between about 5 cm and about 20 cm, between about 10 cm and about 20 cm, or between about 5 cm and about 10 cm. In some embodiments, capillaries 202 have a coiled length (e.g., from one end of a capillary 202 to the other end of the capillary 202) between about 10 cm and about 500 cm, between about 20 cm and about 250 cm, between about 20 cm and about 200 cm, between about 50 cm and about 500 cm, between about 50 cm and about 250 cm, between about 50 cm and about 200 cm, or between about 100 cm and about 200 cm. In some embodiments, each capillary 202 has a diameter of between about 1 µm and about 500 µm, between about 10 µm and about 250 µm, between about 10 µm and about 200 µm, between about 1 µm and about 250 µm, between about 1 µm and about 200 µm, between about 50 µm and about 500 µm, between about 50 µm and about 250 µm, or between about 50 µm and about 200 µm.

In some embodiments, MCC separation device 102 is coupled in downstream flow communication with sample inlet 104, wherein "downstream" refers generally to a direction 114 of gas flow, and "upstream" is generally opposite direction 114. In some embodiments, detector 106 is coupled in downstream flow communication with MCC separation device 102. More specifically, MCC separation device 102 is coupled in flow communication with detector inlet 108. A sample 120 is introduced into sample inlet 104. As described herein, sample 120 includes at least one substance of interest. A carrier gas (not shown) is introduced into sample inlet 104 and/or into MCC separation device 102 to carry sample 120 through MCC separation device 102 as sample gas 122. That is, sample gas 122 includes sample 120 of the substance of interest.

MCC separation device 102 separates the substance of interest in sample gas 122. More particularly, MCC separation device 102 temporally separates the substance of interest in sample gas 122 from other components of sample gas 122. It should be understood that in some embodiments, wherein sample gas 122 includes more than one substance of interest, MCC separation device 102 temporally separates each substance of interest within sample gas 122. MCC separation device 102 then introduces or transfers the separated sample gas 124 to detector inlet 108 for analysis within detector 106 (e.g., within reaction chamber 110). As MCC separation device 102 has temporally separated the components of separated sample gas 124, the substance of interest enters detector inlet 108 at a different time than other components of separated sample gas 124 (e.g., interferents). In some embodiments, as described further herein, the components enter detector inlet 108 with a plurality of seconds therebetween.

Detector 106 analyzes separated sample gas 124. In particular, detector 106 analyzes temporally separated components of separated sample gas 124 as those components are transferred into reaction chamber 110. Subsequently, detector 106 detects the analyzed substance(s) of interest. In some embodiments, computing device 130 of detector 106 includes a pre-programmed library of a plurality of substance(s) and a detection time associated therewith. "Detection time" is generally defined as the time taken for an ionized substance to be detected within detector 106. The detection time is determined based on empirical results of testing of each substance in the library. In some embodiments, the detection time is determined for each substance after separation of a sample gas 122 including the substance. That is, the detection time for the substance in a separated sample ("separated detection time") is different from a detection time for the substance in an unseparated sample ("unseparated detection time"). Each substance within the pre-programmed library has a characteristic separated detection time associated therewith.

It is not uncommon for a substance of interest (e.g., an explosive substance) to have a very similar unseparated detection time (e.g., within milliseconds) as another substance (e.g., an environmental interferent). Without separation of the sample gas 122 including the substance of interest, detector 106 is unable to distinguish substances with such similar unseparated detection times, which lead to false negatives (i.e., a substance of interest not being detected within a sample containing the substance of interest) and/or false positives (i.e., a substance of interest being falsely detected in a sample not containing the substance of interest). In some embodiments, separating sample gas 122 reduces or eliminates certain false negatives and/or false positives. In some embodiments, the components of separated sample gas 124 enter detector 106 at different times. Accordingly, detector 106 distinguishes between substances with similar unseparated detection times because, due to the separation performed by MCC separation device 102, those substances enter detector 106 at different times. The substances thereby have suitably different separated detection times, such that detection of one substance does not interfere with the detection of another substance. In some embodiments, detector 106 distinguishes between substances having separated detection times within about 0.1 sec to about 20 sec of one another, or within about 0.5 sec to about 10 sec of one another, or within about 1 sec to about 5 sec of another, or within about 0.5 sec to about 5 sec of one another, or above about 1 sec of one another. Accordingly, whether one or many substances are included in a single sample, detector 106 readily differentiates between those substances by referencing which substance corresponds to a particular (separated) detection time. That is, detector 106 detects an "unknown" substance having a particular detection time. Detector 106, for example, using computing device 130, references the library of substances to determine which substance corresponds to that detection time. Detector 106 generates an alert or alarm indicating the presence of one or more detected substance(s) of interest. In some embodiments, the alert or alarm includes a visual alert (e.g., text or the lighting of a bulb), a sonic alert, and combinations thereof.

Although detection system 100 is illustrated with sample inlet 104, MCC separation device 102, and detector 106 substantially aligned and in parallel to one another, it should be understood that in alternative embodiments, at least one of sample inlet 104, MCC separation device 102, and/or detector 106 are other than aligned or parallel with another of sample inlet 104, MCC separation device 102, and/or detector 106 without departing from the scope of the disclosure, as long as flow communication therebetween is maintained. For example, in some embodiments, detector inlet 108 is positioned approximately 90° counterclockwise about detector 106 from its illustrated position in FIG. 1. Accordingly, in such an embodiment, detection system 100 is generally forms an "L" shape, wherein MCC separation device 102 and sample inlet 104 are rotated 90° around detector 106. Moreover, it should be understood that, in some embodiments, detection system 100 includes more than one sample inlet 104, MCC separation device 102, and/or detector 106, arranged in series and/or in parallel.

In the illustrated embodiment, detection system 100 is implemented with a generally modular design, wherein sample inlet 104, MCC separation device 102, detector 106, and heating/cooling module 300 are separate, non-integral modules of detection system 100. In some embodiments, MCC separation device 102 and detector 106 are not in thermal communication and as such are not maintained at the same temperature. Accordingly, in some embodiments, detection system 100 includes more than one heating/cooling module 300 to separately heat and cool each of MCC separation device 102 and detector 106.

In the illustrated embodiment, heating/cooling module 300 is configured to heat and cool MCC separation device 102. In some embodiments, hot block 302 and cold block 304 are spaced from MCC separation device 102 in an initial, distal, and/or inactive state (as illustrated in FIG. 3). Hot block 302 is operatively coupled to first linear actuator 306, and cold block 304 is operatively coupled to second linear actuator 308. In some embodiments, the temperature of hot block 302 is maintained by a separate heating element 320 in thermal communication with hot block 302 when hot block 302 is positioned distally from MCC separation device 102. In some embodiments, separate heating element 320 is interior or exterior to detection system 100. In some embodiments, the temperature of cold block 304 is maintained by a separate cooling element 322 in thermal communication with cold block 304 when cold block 304 is positioned distally from MCC separation device 102. For example, in some embodiments, a plurality of fins 324 thermally couple the separate cooling element 322 to cold block 304. In some embodiments, separate cooling element 322 is interior or exterior to detection system 100.

To heat MCC separation device, first linear actuator 306 translates hot block 302 towards MCC separation device 102 to position hot block 302 adjacent to and/or in thermal communication with MCC separation device 102. More specifically, first linear actuator 306 moves hot block 302 along a linear axis 310 proximal to MCC separation device 102. Hot block 302 heats MCC separation device 102 to a heated temperature, as described elsewhere herein, for separation of sample gas 122. In some embodiments, hot block 302 maintains MCC separation device 102 at the heated temperature for a duration of the separation of sample gas 122 and/or for any period of time thereafter (e.g., during analysis of separated sample gas 124 and/or detection of the substance of interest).

Once the separation of sample gas 122 is complete and/or the MCC separation device 102 no longer need be at the heated temperature, first linear actuator 306 moves hot block 302 distally from MCC separation device 102. To cool MCC separation device 102 to an initial and/or a non-heated temperature, second linear actuator 308 translates cold block 304 towards MCC separation device 102 to position cold block 304 adjacent to and/or in thermal communication with MCC separation device 102. More specifically, second linear actuator 308 moves cold block 304 along linear axis 310 proximal to MCC separation device 102. Cold block 304 cools MCC separation device 102 to the initial and/or the non-heated temperature, as described elsewhere herein. In some embodiments, cold block 304 maintains MCC separation device 102 at the initial and/or non-heated temperature for any duration of time. Alternatively or additionally, once cold block 304 has cooled MCC separation device 102 to the initial and/or non-heated temperature, in some embodiments cold block 304 is moved away from MCC separation device 102. Second linear actuator 308 moves cold block 304 distally from MCC separation device 102. In some embodiments, MCC separation device 102 is cooled to the initial and/or non-heated temperature by ambient air (not specifically shown).

It should be understood that in some embodiments, heating/cooling module 300 includes any number of hot blocks 302 and/or cold blocks 304. For example, in some embodiments, heating/cooling module 300 includes a plurality of hot blocks 302 and a plurality of cold blocks 304. In some embodiments, heating/cooling module 300 includes any number of linear actuators 304, 306. In some embodiments, each block 302, 304 of heating/cooling module 300 is moved using an individual actuator 304, 306. In some embodiments, multiple blocks 302, 304 are moved using a single actuator 304, 306. In some embodiments, any number of actuators control movement of any number of hot/cold blocks. Furthermore, in some embodiments, heating/cooling module 300 includes heating and/or cooling elements other than and/or in addition to hot/cold blocks 302, 304. For example, in some embodiments, heating elements include at least one of a resistive element, an insulative element, a thermal conductor, a radiant heater, a thermoelectric heater and combinations thereof.

In some embodiments, to heat MCC separation device 102, the heating element is positioned in thermal communication with MCC separation device 102. In some embodiments, the heating element is coupled to MCC separation device 102, in direct or indirect physical contact therewith. In some embodiments, cooling elements include at least one of a fan, a radiant cooler, cooling air, a coolant fluid, a Peltier cooler, a thermoelectric cooler and combinations thereof. To cool MCC separation device 102, in some embodiments, the cooling element is positioned in thermal communication with MCC separation device 102. In some embodiments, the cooling element is coupled to MCC separation device 102, in direct or indirect physical contact therewith.

As used herein, the term "computer" and related terms, e.g., "computing device", are not limited to integrated circuits referred to in the art as a computer, but broadly refers to a microcontroller, a microcomputer, a programmable logic controller (PLC), an application specific integrated circuit, and other programmable circuits, and these terms are used interchangeably herein. Further, as used herein, the terms "software" and "firmware" are interchangeable, and include any computer program stored in memory for execution by personal computers, workstations, clients and servers.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

In one embodiment, computing device 130 includes a memory device 132 and a processor 134 operatively coupled to the memory device 132 for executing instructions. In some embodiments, executable instructions are stored in the memory device 132. Computing device 130 is configurable to perform one or more operations described herein by the programming processor 134. For example, in some embodiments, processor 134 is programmed by encoding an operation as one or more executable instructions and providing the executable instructions in memory device 132. In the exemplary embodiment, memory device 132 is one or more devices that enable storage and retrieval of information such as executable instructions and/or other data. Memory device 132 includes one or more computer readable media in some embodiments.

Memory device 132 is configured to store the pre-programmed library of substances and associated detection times, alarm limits, detection history, calibration profiles and history for detector 106, and/or any other type data in some embodiments.

In the exemplary embodiment, computing device 130, including memory device 132, includes, without limitation, sufficient computer-readable/executable instructions, sufficient data and data structures, algorithms, and commands to facilitate detection of sub stance(s) of interest from the separated sample gas 124 within reaction chamber 110.

In the exemplary embodiment, substance detection system 100 further includes an operator presentation and/or control interface 136 coupled to computing device 130. Interface 136 presents data, such as detection time(s) of components of separated sample gas 124 and/or various alerts of alarms. In some embodiments, interface 136 includes one or more display devices. In some embodiments, interface 136 presents an audible and/or graphical notification upon detection of a substance of interest. Also, in some embodiments, interface 136 facilitates control of computing device 130 and manual data input into computing device 130. Furthermore, in some embodiments, computing device 130 is coupled in communication with one or more other devices, such as another computing device 130, locally or remotely. As such, in some embodiments, substance detection system 100 is networked with other systems and devices such that data transmitted across portions of system 100 is accessed by any device capable of accessing computing device 130 including, without limitation, desktop computers, laptop computers, and personal digital assistants (PDAs) (neither shown).

Figure 4:
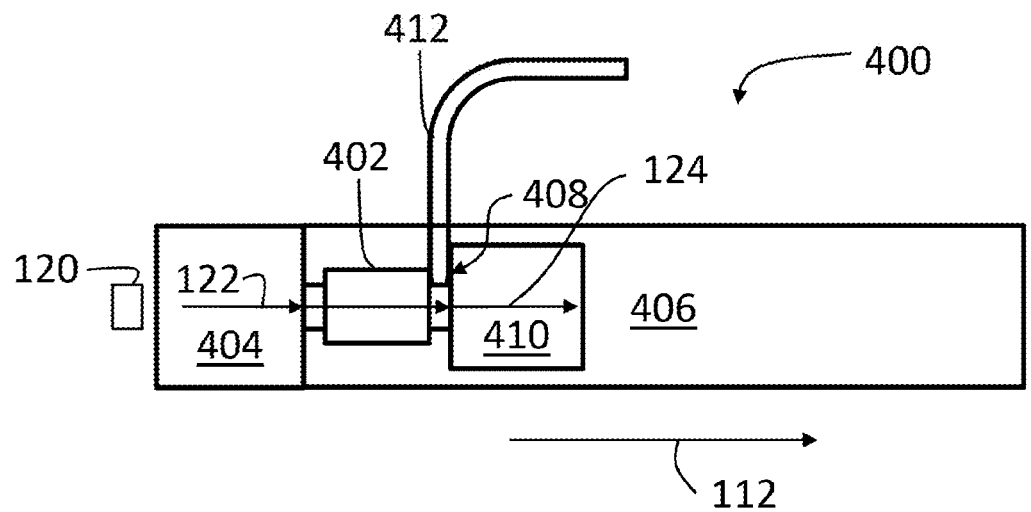
FIG. 4 is an exemplary embodiment of a schematic diagram of an alternative detection system including an MCC separation device in accordance with the present disclosure.

FIG. 4 is an exemplary embodiment of a schematic diagram of an alternative detection system 400 including an MCC separation device 402 in accordance with the present disclosure. Detection system 400 includes a sample inlet 404, MCC separation device 402, and a detector 406. Detector 406 includes an inlet 408 and a reaction chamber 410. Inlet 408 may be referred to as "reaction chamber inlet" 408. Detector 406 further includes a purge line 412 coupled upstream of reaction chamber 410. Sample inlet 404 is coupled in flow communication with MCC separation device 402, and MCC separation device 402 is coupled in flow communication with detector 406. Purge line 412 is coupled in flow communication with MCC separation device 402.

In detection system 400, MCC separation device 402 is integral to detector 406. In some embodiments, MCC separation device 402 replaces an existing transfer line (not shown) in detector 406, such that providing MCC separation device 402 within detector 406 adds little to no excess volume to detector 406. Moreover, MCC separation device 402 is insulated within detector 406, such that MCC separation device 402 and detector 406 are maintained at the same temperature with respect to the other of MCC separation device 402 and detector 406. That is, in some embodiments, detection system 400 includes any additional heating/cooling modules to heat/cool MCC separation device 402 as MCC separation device 402 is heated/cooled indirectly in accordance with heating/cooling of detector 406. In some embodiments, detector system 400 includes a separate heating/cooling module (not shown in FIG. 4) for heating/cooling of MCC separation device 402.

Similar to the separation process described above with respect to FIG. 1, a sample 120 is introduced into sample inlet 404. Sample 120 includes at least one substance of interest. A carrier gas (not shown) is introduced into sample inlet 404 and/or into MCC separation device 402 to carry sample 120 through MCC separation device 402 as sample gas 122. That is, sample gas 122 includes sample 120 of the substance of interest.

MCC separation device 402 separates the substance of interest in sample gas 122. More particularly, MCC separation device 402 temporally separates the substance of interest in sample gas 122 from other components of sample gas 122. It should be understood that wherein sample gas 122 includes more than one substance of interest, MCC separation device 402 temporally separates each substance of interest within sample gas 122. In some embodiments, certain substances ("contaminants") contaminate detector 406 if those contaminants are permitted to enter detector 406. By temporally separating components of sample gas 122, MCC separation device 402 transfers a portion of separated sample gas 124 containing these contaminants to purge line 412 for exhausting from detection system 400 prior to introduction into detector 406. For example, a total analysis time may be about 10 sec (i.e., sample gas 122 is introduced to MCC separation device 402 from t=0 sec to t=10 sec). Explosive substances (substances of interest) are temporally separated within MCC separation device 402 within about 1-6 sec. Accordingly, from about 0-1 sec, and after 6 sec, separated sample gas 124 will be exhausted through purge line 412 to exhaust at least some contaminants before they enter detector 406. During the 1-6 sec period of the analysis, separated sample gas 124 will enter detector 406.

MCC separation device 402 then introduces or transfers the separated sample gas 124 to reaction chamber inlet 408 for analysis within detector 406 (e.g., within reaction chamber 410). As MCC separation device 402 has temporally separated the components of separated sample gas 124, the substance of interest enters inlet 408 at a different time than other components of separated sample gas 124 (e.g., interferents). In some cases, as described further herein, the components enter inlet 408 with a plurality of seconds therebetween. Detector 406 analyzes separated sample gas 124. In particular, detector 406 analyzes temporally separated components of separated sample gas 124 as those components are transferred into reaction chamber 410. Subsequently, detector 406 detects the analyzed substance(s) of interest. Detector 406 generates an alert or alarm indicating the presence of the substance(s) of interest in some embodiments.

EXAMPLES

The following examples describe or illustrate various embodiments of the present disclosure. Other embodiments within the scope of the appended claims will be apparent to a skilled artisan considering the specification or practice of the disclosure as described herein. It is intended that the specification, together with the Examples, be considered exemplary only, with the scope and spirit of the disclosure being indicated by the claims, which follow the Examples.

Example 1

Figure 5A:
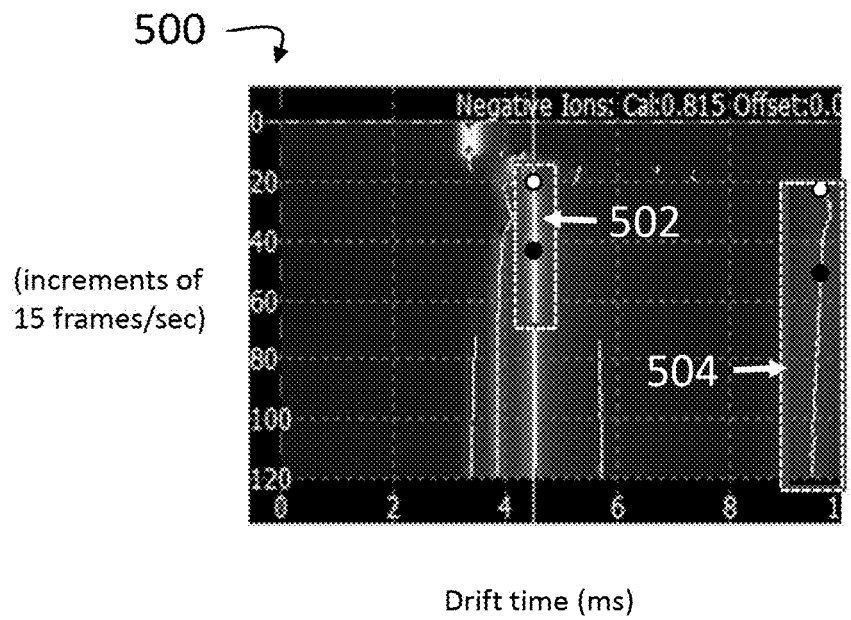
FIG. 5A is an exemplary graph depicting temporal interference between a substance of interest and an interferent in an unseparated sample gas within a detector reaction chamber.
Figure 5B:
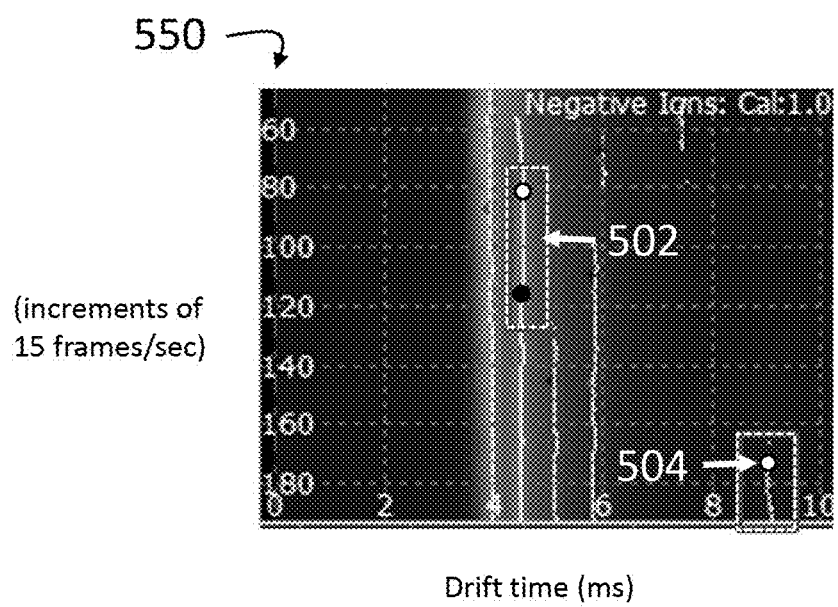
FIG. 5B is an exemplary graph depicting a substance of interest temporally separated from an interferent within the detector reaction chamber.

Example 1 is an exemplary embodiment of the reduction of false negatives using the detection systems and methods disclosed herein. FIG. 5A is an exemplary graph 500 depicting temporal interference between a substance of interest 502 and an interferent 504 in an unseparated sample gas within a detector reaction chamber. FIG. 5B is an exemplary graph 550 depicting the substance of interest 502 temporally separated from the interferent 504 within the detector reaction chamber. For both graph 500 and graph 550, as well as further Examples herein, the x-axis represents a signature or identity of the substance being detected (a "drift time"), and the y-axis represents increments of a number of "scans" performed by the detector per second (or any unit of time). More specifically, in the exemplary embodiment, the units of the y-axis represent 15 scans/sec (i.e., "60" represents a time of about 4 sec). Moreover, each line represents a detected substance, each "open" dot represents the time at which a highest slope or highest increase of the substance (corresponding to the line on which the dot is located) was detected, and each "filled" dot represents the time at which a maximum amount of the substance was detected. Each "box" surrounds both the open dot and the filled dot, and generally represents "detection" of the corresponding substance.

In this example, the substance of interest 502 is urea nitrate (UN), and the interferent 504 is a phthalate substance. Phthalate substances are common interferents from vinyl substrate sample swabs employed, for example, in airport security sample collection. Graph 500 depicts how the substance of interest 502 and the interferent 504 were detected by the detector at approximately the same (unseparated) detection time (about 2 sec), when an unseparated sample gas containing both substances was introduced into the detector. In particular, the substance of interest 502 and the interferent 504 competed for charge accumulation ("ionization") within the detector. Moreover, as described above, the substance of interest 502 and the interferent 504 had similar unseparated detection times. A false negative was therefore generated, as the detector did not recognize the presence of the substance of interest 502 beyond the interferent 504 due to ion suppression.

Graph 550 depicts how separation of the sample gas prevented this interference. Specifically, the substance of interest 502 was detected about 5 sec from an initial time ($t_0$ or t=0) at which the sample gas is introduced into the detector, and the interferent 504 was detected about 6 sec later (about 11 sec from when the sample gas was introduced into the detector). The separated detection times of the substance of interest 502 (5 sec) and the interferent 504 (11 sec) were substantially different, such that the detector more readily differentiated between the substance of interest 502 and the interferent 504 and more readily identified the substance of interest 502 in the analyzed sample.

Example 2

Figure 6A:
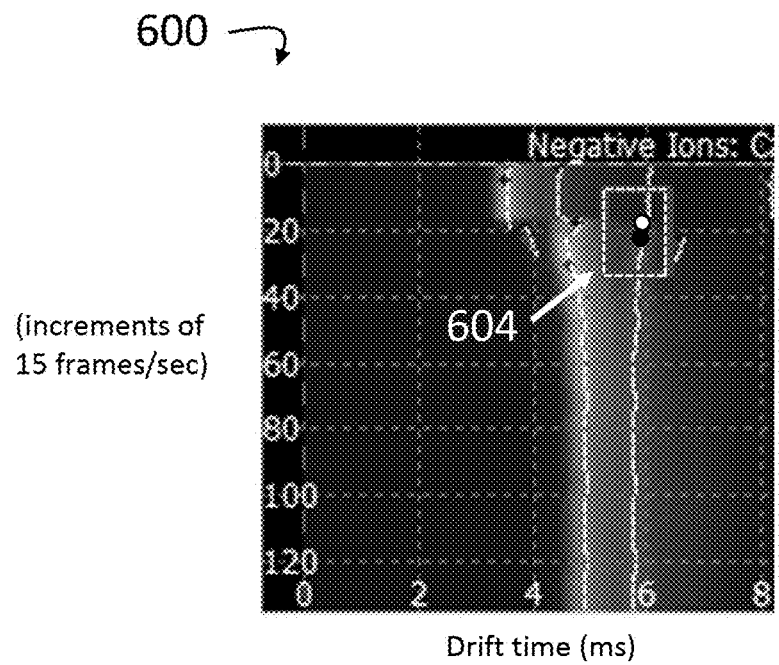
FIG. 6A is an exemplary graph depicting an interferent in a separated sample gas within a detector reaction chamber.
Figure 6B:
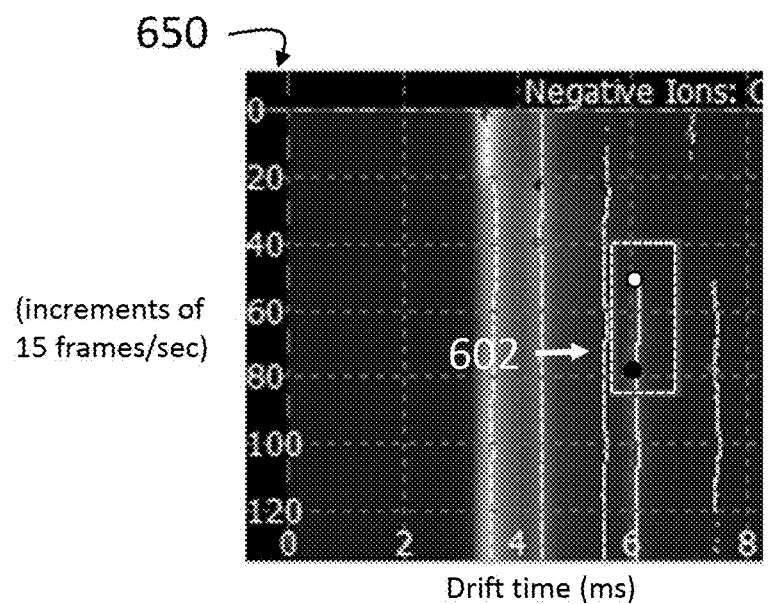
FIG. 6B is an exemplary graph depicting a substance of interest in a separated sample gas within the detector reaction chamber.

Example 2 is an exemplary embodiment of the reduction of false positives using the detection systems and methods disclosed herein. FIG. 6A is an exemplary graph 600 depicting an interferent 604 in a separated sample gas within a detector reaction chamber. FIG. 6B is an exemplary graph 650 depicting a substance of interest 602 in a separated sample gas within the detector reaction chamber. The substance of interest 602 and the interferent 604 are depicted on separate graphs for clarity and ease of understanding.

In this example, the substance of interest 602 was trinitrotoluene (TNT), and the interferent 604 was a hand swab compound found in common hand sample swabs employed, for example, in airport security sample collection. The interferent 604 and the substance of interest 602 had very similar drift times (very nearly 6 ms, shown on the x-axis). Accordingly, the detector "false alarmed" (i.e., generate a false positive) upon detection of the interferent 604. Similar false positives were generated with other compounds having a very similar drift time with another substance of interest, for example, sorbitol (an interferent) and Research Department explosive (RDX) (a substance of interest). Separating a sample gas containing either of the interferent 604 and/or the substance of interest 602 reduced or eliminated these false positives by identifying a separated detection time for each substance 602, 604 that is suitably dissimilar from the other substance 602, 604 such that the detector more readily distinguished therebetween.

With reference to graph 600, the detector detected a particular substance having a drift time very near 6 ms at a detection time of about 1.5 sec. The detector referenced a library of substances and determined that such a drift time and detection time were associated with interferent 604. Accordingly, the detector did not generate an alarm, thus eliminating the false positive that had previously occurred.

With reference to graph 650, the detector detected a particular substance having a drift time very near 6 ms at a detection time of about 3 sec. The detector referenced the library of substances and determined that such a drift time and detection time were associated with substance of interest 602. Accordingly, the detector generated an alarm indicating the detection of the substance of interest 602. The detector more readily differentiated between the substance of interest 602 and the interferent 604 and more readily identified whether merely an interferent 604 or rather the substance of interest 602 was present in the analyzed sample.

Example 3

Figure 7A:
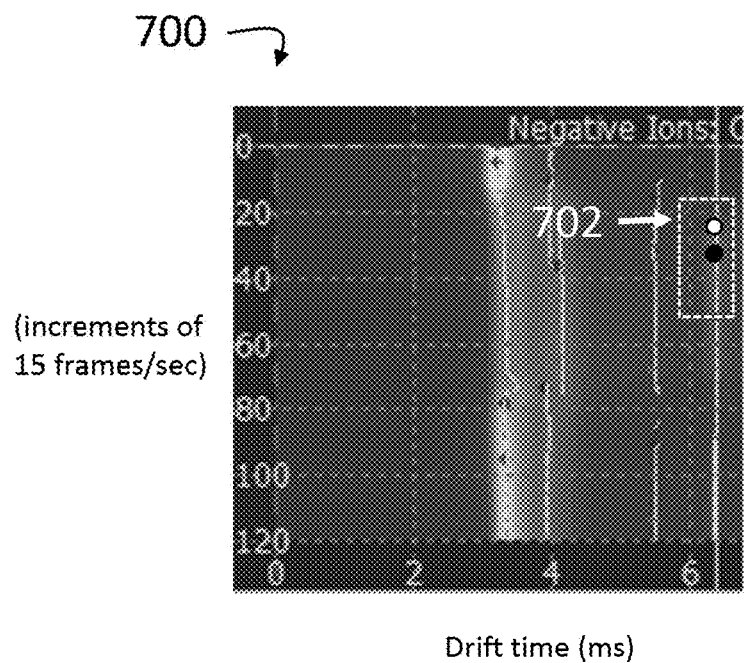
FIG. 7A is an exemplary graph depicting a first substance of interest in an unseparated sample gas within a detector reaction chamber.
Figure 7B:
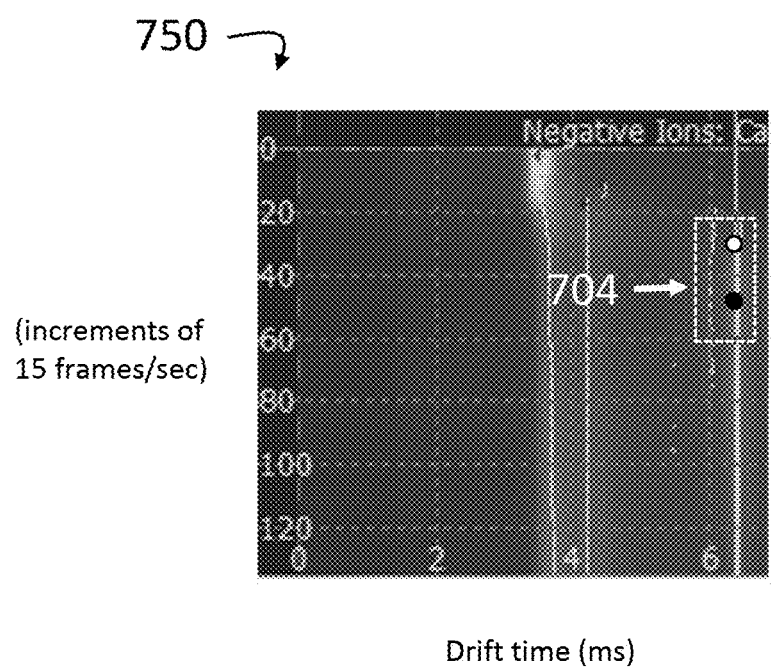
FIG. 7B is an exemplary graph depicting a second substance of interest in an unseparated sample gas within the detector reaction chamber.
Figure 7C:
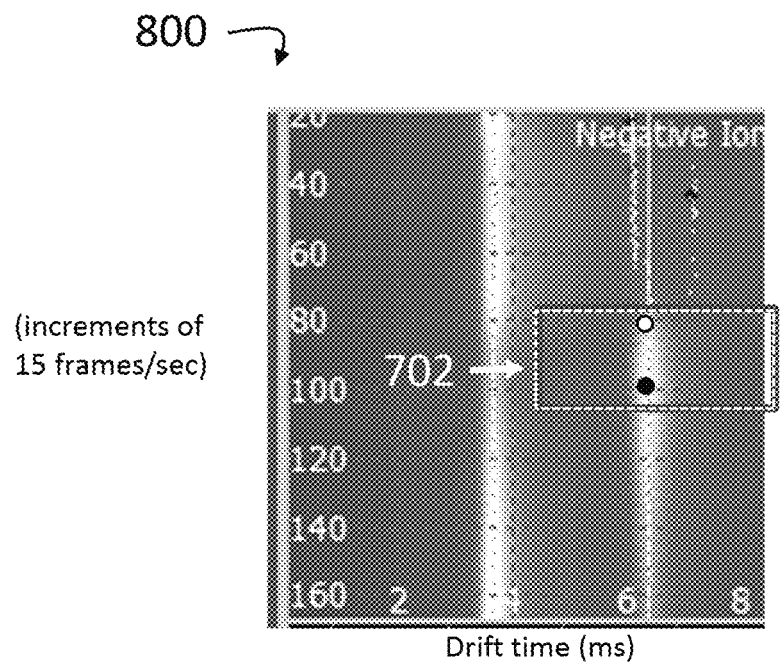
FIG. 7C is an exemplary graph depicting the first substance of interest in a separated sample gas within the detector reaction chamber.
Figure 7D:
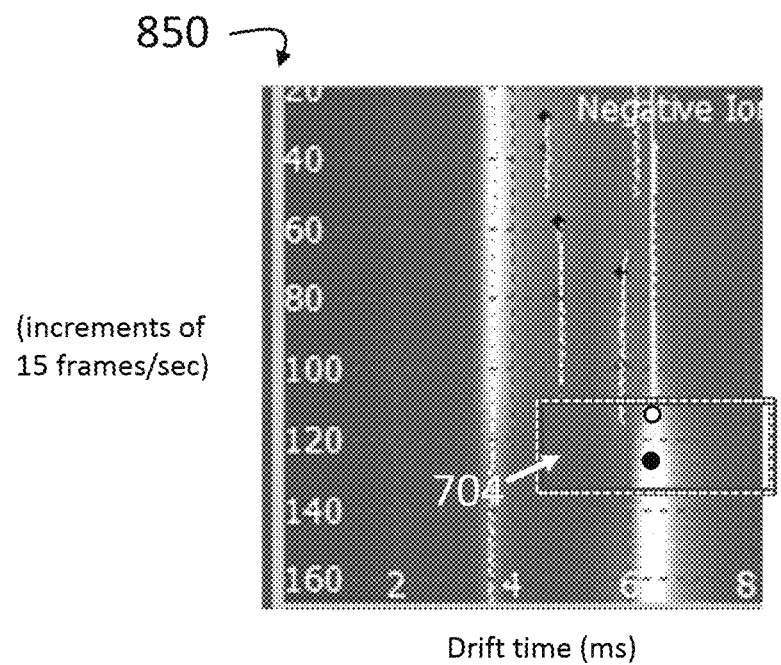
FIG. 7D is an exemplary graph depicting the second substance of interest in a separated sample gas within the detector reaction chamber.

Example 3 is an exemplary embodiment of the improved selectivity between substances of interest using the detection systems and methods disclosed herein. FIG. 7A is an exemplary graph 700 depicting a first substance of interest 702 in an unseparated sample gas within a detector reaction chamber. FIG. 7B is an exemplary graph 750 depicting a second substance of interest 704 in an unseparated sample gas within the detector reaction chamber. FIG. 7C is an exemplary graph 800 depicting the first substance of interest 702 in a separated sample gas within the detector reaction chamber. FIG. 7D is an exemplary graph 850 depicting the second substance of interest 704 in a separated sample gas within the detector reaction chamber. The first substance of interest 702 and the second substance of interest 704 are depicted on separate graphs for clarity and ease of understanding.

In this example, the first substance of interest 702 was RDX, and the second substance of interest 704 was trinitrophenylmethylnitramine (Tetryl). Both substances of interest 702, 704 are explosive compounds, and both substances of interest 702, 704 had very similar drift times (about 6.1 ms, shown on the x-axis). Accordingly, in previous systems without separation of the sample gas, an "RDX/Tetryl" alarm was generated when either or both substance(s) of interest 702, 704 were detected. That is, those systems could not distinguish between the two substances of interest 702, 704.

With reference to graph 700, when a sample gas including the first substance of interest 702 was introduced into the detector, a substance having a drift time of about 6.1 ms and a detection time of about 1.5 sec was detected. The detector referenced a library of (unseparated) substances and determined that such a drift time and unseparated detection time were associated with both substances of interest 702, 704. The detector generated an alarm identifying detection of both the first and second substances of interest 702, 704.

Similarly, with reference to graph 750, when a sample gas including the second substance of interest 704 was introduced into the detector, a substance having a drift time of about 6.1 ms and a detection time of about 1.5 sec was detected. The detector referenced a library of (unseparated) substances and determined that such a drift time and unseparated detection time were associated with both substances of interest 702, 704. The detector generated an alarm identifying detection of both the first and second substances of interest 702, 704.

Separating a gas sample including one or both substance(s) of interest 702, 704 provided suitable selectivity or sensitivity such that the particular substance(s) of interest 702 and/or 704 were individually detected and identified. Although Example 3 used RDX/Tetryl as the illustrative substances of interest, it should be readily understood that the same principles described herein are applied to other substances of interest, such as RDX/HMX and/or TNT/NG.

With reference to graph 800, when a separated sample gas including the first substance of interest 702 was introduced into the detector, a substance having a drift time of about 6.1 ms and a separated detection time of about 5 sec was detected. The detector referenced the library of (separated) substances and determined that such a drift time and separated detection time were associated with the first substance of interest 702. The detector generated an alarm identifying detection of only the first substance of interest 702.

Similarly, with reference to graph 850, when a separated sample gas including the second substance of interest 704 was introduced into the detector, a substance having a drift time of about 6.1 ms and a separated detection time of about 7.5 sec was detected. The detector referenced the library of (separated) substances and determined that such a drift time and separated detection time were associated with the second substance of interest 704. The detector generated an alarm identifying detection of only the second substance of interest 704. The detector more readily differentiated between the first and second substances of interest 702, 704 and more accurately identified whether one or both of the first and second substances of interest 702, 704 were present in the analyzed sample.

Exemplary embodiments of detection systems for determining the presence of substances of interest, and methods of operating such systems are not limited to the specific embodiments described herein, but rather, components of systems and/or steps of the methods may be utilized independently and separately from other components and/or steps described herein. For example, the methods may also be used in combination with other systems requiring determining the presence of substances of interest, and are not limited to practice with only the substance detection systems and methods as described herein. Rather, the exemplary embodiment can be implemented and utilized in connection with many other substance detection applications that are currently configured to determine the presence of substances of interest.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

Some embodiments involve the use of one or more electronic or computing devices. Such devices typically include a processor or controller, such as a general purpose central processing unit (CPU), a graphics processing unit (GPU), a microcontroller, a reduced instruction set computer (RISC) processor, an application specific integrated circuit (ASIC), a programmable logic circuit (PLC), and/or any other circuit or processor capable of executing the functions described herein. The methods described herein may be encoded as executable instructions embodied in a computer readable medium, including, without limitation, a storage device and/or a memory device. Such instructions, when executed by a processor, cause the processor to perform at least a portion of the methods described herein. The above examples are exemplary only, and thus are not intended to limit in any way the definition and/or meaning of the term processor.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system for detecting a substance of interest, the system comprising:
    a sample inlet, configured to receive a sample including at least one substance of interest;
    an analysis device including a multi-capillary column (MCC) separation device located therein, the MCC separation device coupled in flow communication with the sample inlet and configured to separate the at least one substance of interest, wherein the MCC separation device is configured to transfer the at least one separated substance of interest into the analysis device for analysis at a flow rate of from about 10 ml/min to about 500 ml/min; and wherein the analysis device is configured to perform an analysis of the at least one separated substance of interest transferred from the MCC separation device; and
    a purge line in flow communication with the MCC separation device configured to purge contaminants therefrom.

2. The system of claim 1, wherein the MCC separation device is configured to transfer the at least one substance of interest into the analysis device at a flow rate of from about 50 ml/min to about 200 ml/min.

3. The system of claim 1, wherein the MCC separation device is further configured to temporally separate the at least one substance of interest.

4. The system of claim 3, wherein the sample includes more than one substance of interest.

5. The system of claim 4, wherein the MCC separation device is configured to transfer the substances of interest into the analysis device at different times.

6. The system of claim 1, wherein the at least one substance of interest includes at least one of nitro, nitrate, triacetone triperoxide (TATP), ammonium nitrate (AN), ammonium nitrate fuel oil (ANFO), urea nitrate (UN), 2,4,6-trinitrophenylmethylnitramine (tetryl), trinitrotoluene (TNT), ethylene glycol dinitrate (EGDN), nitroglycerin (NG), pentaerythritol tetranitrate (PETN), high melting explosive (HMX), Research Department Explosive (RDX), black powder, cocaine, 3,4-methylenedioxy-N-methylamphetamine (MDMA), an opiate, diazepam and combinations thereof.

7. The system of claim 1, wherein the analysis device includes at least one of an ion mobility spectrometer (IMS), an ion trap mobility spectrometer (ITMS), a drift spectrometer (DS), a non-linear drift spectrometer, a field ion spectrometer (FIS), a radio frequency ion mobility increment spectrometer (IMIS), a field asymmetric ion mobility spectrometer (FAIMS), an ultra-high-field FAIMS, a differential ion mobility spectrometer (DIMS) and a differential mobility spectrometer (DMS), a traveling wave ion mobility spectrometer, a semiconductor gas sensor, a raman spectrometer, a laser diode detector, a mass spectrometer (MS), an electron capture detector, a photoionization detector, a chemiluminescence-based detector, an electrochemical sensor, an infrared spectrometer, a lab-on-a-chip detector and combinations thereof.

8. The system of claim 1, further comprising at least one of a heating element and a cooling element in thermal communication with the MCC separation device.

9. The system of claim 8, wherein the MCC separation device is heated to a temperature of between about 20° C. to about 300° C.

10. A method for detecting a substance of interest, the method comprising:
separating at least one substance of interest from a sample, wherein the at least one substance of interest is separated in a multi-capillary column (MCC);
separating at least one contaminant from the sample, wherein the at least one contaminant is separated in the MCC;
transferring the at least one contaminant from the MCC into a purge line; and
transferring the at least one separated substance of interest from the MCC into a detector, wherein the at least one separated substance of interest is transferred into the detector at a flow rate of from about 10 ml/min to about 500 ml/min, wherein the detector performs an analysis of the at least one separated substance of interest and detects the at least one substance of interest.

11. The method of claim 10, wherein the MCC is configured to transfer the at least one substance of interest into the detector at a flow rate of from about 50 ml/min to about 200 ml/min.

12. The method of claim 10, wherein the MCC is further configured to temporally separate the at least one substance of interest.

13. The method of claim 12, wherein the sample includes more than one substance of interest.

14. The method of claim 13, wherein the MCC is configured to transfer the substances of interest into the detector at different times.

15. The method of claim 10, wherein the at least one substance of interest includes at least one of nitro, nitrate, triacetone triperoxide (TATP), ammonium nitrate (AN), ammonium nitrate fuel oil (ANFO), urea nitrate (UN), 2,4,6-trinitrophenylmethylnitramine (tetryl), trinitrotoluene (TNT), ethylene glycol dinitrate (EGDN), nitroglycerin (NG), pentaerythritol tetranitrate (PETN), high melting explosive (HMX), Research Department Explosive (RDX), black powder, cocaine, 3,4-methylenedioxy-N-methylamphetamine (MDMA), an opiate, diazepam and combinations thereof.

16. The method of claim 10, wherein the detector includes at least one of an ion mobility spectrometer (IMS), an ion trap mobility spectrometer (ITMS), a drift spectrometer (DS), a non-linear drift spectrometer, a field ion spectrometer (FIS), a radio frequency ion mobility increment spectrometer (IMIS), a field asymmetric ion mobility spectrometer (FAIMS), an ultra-high-field FAIMS, a differential ion mobility spectrometer (DIMS) and a differential mobility spectrometer (DMS), a traveling wave ion mobility spectrometer, a semiconductor gas sensor, a raman spectrometer, a laser diode detector, a mass spectrometer (MS), an electron capture detector, a photoionization detector, a chemiluminescence-based detector, an electrochemical sensor, an infrared spectrometer, a lab-on-a-chip detector and combinations thereof.

17. The method of claim 10, further comprising at least one of a heating element and a cooling element in thermal communication with the MCC.

18. The method of claim 17, wherein the MCC is heated to a temperature of between about 20° C. to about 300° C.

19. The method of claim 10, wherein into the detector is located within the detector.

* * * * *